(12) United States Patent
Sabaria

(10) Patent No.: US 9,326,869 B2
(45) Date of Patent: *May 3, 2016

(54) METHOD FOR EXPANSION AND DEVELOPMENT OF POLYMERIC STRUCTURES INCLUDING STENTS

(71) Applicant: Arterial Remodeling Technologies, S.A., Noisy le Roi (FR)

(72) Inventor: Patrick Sabaria, Saint Nom la Breteche (FR)

(73) Assignee: Arterial Remodeling Technologies, S.A. (FR)

( * ) Notice: Subject to any disclaimer, the term of this patent is extended or adjusted under 35 U.S.C. 154(b) by 186 days.

This patent is subject to a terminal disclaimer.

(21) Appl. No.: 14/143,374

(22) Filed: Dec. 30, 2013

(65) Prior Publication Data

US 2014/0114397 A1    Apr. 24, 2014

Related U.S. Application Data

(63) Continuation of application No. 12/282,738, filed as application No. PCT/IB2007/003195 on Oct. 24, 2007, now Pat. No. 8,636,787.

(60) Provisional application No. 60/854,075, filed on Oct. 25, 2006.

(51) Int. Cl.
*A61F 2/82* (2013.01)
*A61L 31/06* (2006.01)

(52) U.S. Cl.
CPC . *A61F 2/82* (2013.01); *A61L 31/06* (2013.01); *A61F 2210/0023* (2013.01)

(58) Field of Classification Search
CPC .............. A61F 2/06; A61F 2/82; A61F 2/94; A61F 2/958; A61F 2210/0004; A61F 2210/0023; A61F 2210/0042; A61L 31/06
See application file for complete search history.

(56) References Cited

U.S. PATENT DOCUMENTS

| | | | |
|---|---|---|---|
| 5,292,321 A * | 3/1994 | Lee | A61B 17/22 606/198 |
| 5,565,215 A | 10/1996 | Gref et al. | |
| 5,800,516 A | 9/1998 | Fine et al. | |
| 5,957,975 A | 9/1999 | Lafont et al. | |
| 6,607,553 B1 | 8/2003 | Healy et al. | |
| 7,044,964 B2 | 5/2006 | Jang et al. | |
| 2005/0049672 A1 | 3/2005 | Murphy | |
| 2006/0004440 A1 | 1/2006 | Stinson | |
| 2008/0051866 A1 | 2/2008 | Chen et al. | |

FOREIGN PATENT DOCUMENTS

WO    2005096992    10/2005

* cited by examiner

*Primary Examiner* — Sarah W Aleman
(74) *Attorney, Agent, or Firm* — Tarolli, Sundheim, Covell & Tummino LLP

(57) ABSTRACT

The invention is to methods of deploying polymeric biodegradable or non biodegradable stents by use of stepwise creases in the pressure placed upon the inner diameter of the stent to slowly increase the stent diameter. In one embodiment, the pressure on the interior stent diameter is slowly increased. The stent is allowed to acclimate to this diameter for a set period of time, and then the pressure is again increased. This series of steps continues until the stent reaches its final diameter and a final period of acclimatization is maintained prior to the removal of the deployment/delivery device.

24 Claims, 1 Drawing Sheet

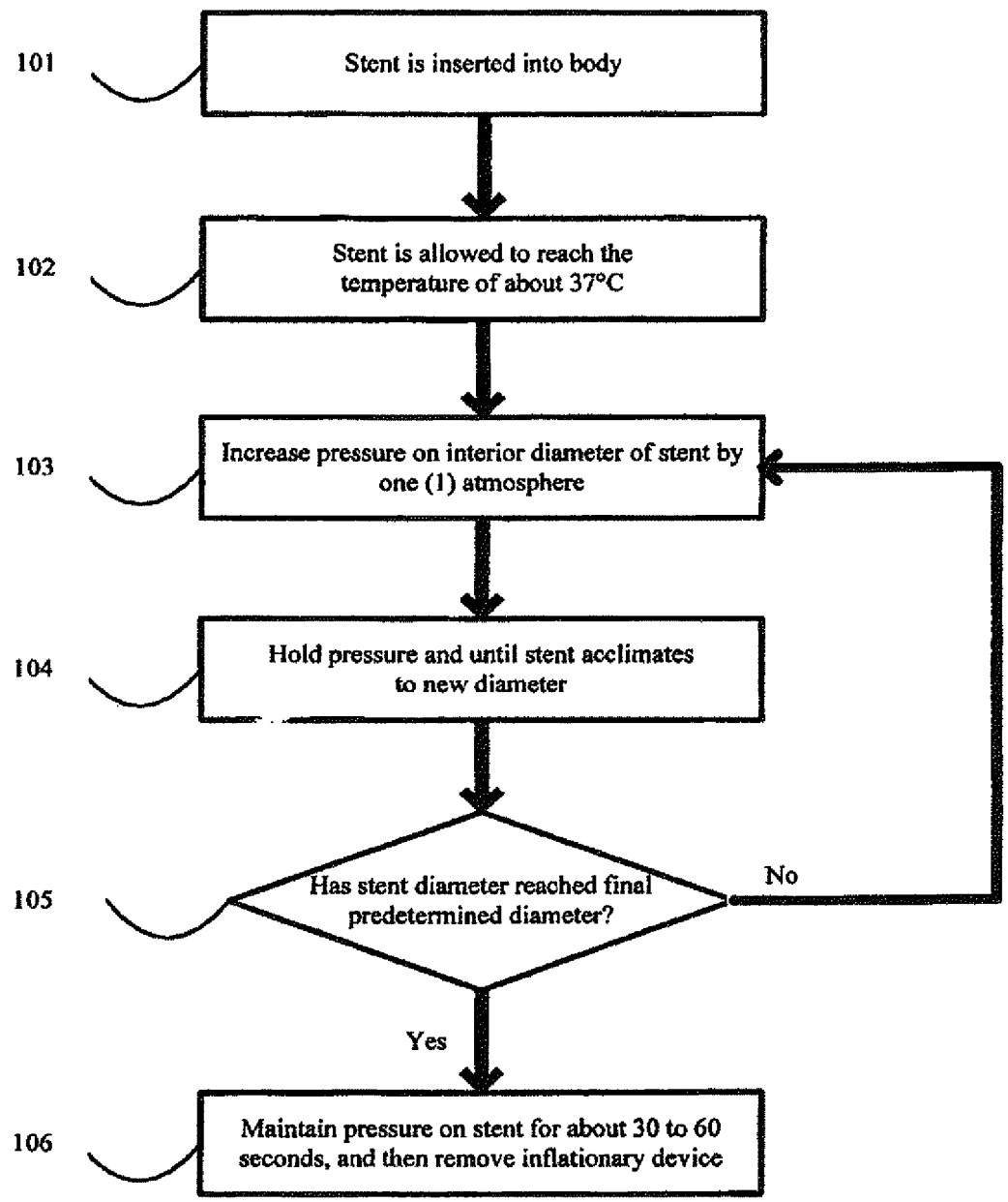

US 9,326,869 B2

METHOD FOR EXPANSION AND DEVELOPMENT OF POLYMERIC STRUCTURES INCLUDING STENTS

RELATED APPLICATIONS

The present application is a continuation of U.S. patent application Ser. No. 12/282,738, filed Sep. 12, 2008, which claims priority to U.S. Provisional Patent Application No. 60/854,075, filed Oct. 25, 2006. Each of the aforementioned applications is incorporated by reference herein in its entirety.

BACKGROUND OF THE INVENTION

The use of stents in various surgical, interventional cardiology, and radiology procedures has quickly become accepted medical practice as experience with stent devices accumulates and as the advantages of stents become more widely recognized. Stents are often used in body lumens to maintain open passageways such as the prostatic urethra, the esophagus, the biliary tract, intestines, and various coronary arteries and veins, as well as more remote cardiovascular vessels such as the femoral artery.

Stents are often used to treat atherosclerosis, a disease in which vascular lesions or plaques consisting of cholesterol crystals, necrotic cells, lipid pools, excess fiber elements and calcium deposits accumulate in the walls of an individual's arteries. One of the most successful procedures for treating atherosclerosis is to insert a deflated balloon within the lumen, adjacent the site of the plaque or atherosclerotic lesion. The balloon is then inflated to put pressure on and "crack" the plaque. This procedure increases the cross-sectional area of the lumen of the artery. Unfortunately, the pressure exerted also traumatizes the artery, and in 30-40% of the cases, the vessel either gradually renarrows or recloses at the locus of the original stenotic lesion. This renarrowing is known as restenosis.

A common approach to prevent restenosis is to deploy a metallic stent to the site of the stenotic lesion. Although metallic stents have the mechanical strength necessary to prevent the retractile form of restenosis, their presence in the artery can lead to biological problems including vasospasm, compliance mismatch, and even occlusion. Moreover, there are inherent, significant risks from having a metal stent permanently implanted in the artery, including erosion of the vessel wall. The stents may also migrate on occasion from their initial insertion location raising the potential for stent-induced blockage. Metal stents, especially if migration occurs, cause irritation to the surrounding tissues in a lumen. Also, since metals are typically much harder and stiffer than the surrounding tissues in a lumen, this may result in an anatomical or physiological compliance mismatch, thereby damaging tissue or eliciting unwanted biologic responses. In addition, the constant exposure of the stent to the blood can lead to thrombus formation within the blood vessel. Stents also allow the cellular proliferation associated with the injured arterial wall to migrate through the stent mesh, where the cells continue to proliferate and eventually lead to the narrowing of the vessel. Further, metal stents typically have some degree of negative recoil. Finally, metallic stents actually prevent or inhibit the natural vascular remodeling that can occur in the organism by rigidly tethering the vessel to a fixed, maximum diameter.

Because of the problems of using a metallic stent, others have recently explored use of bioabsorbable and biodegradable materials stents. The conventional bioabsorbable or bioresorbable materials from which such stents are made are selected to absorb or degrade over time. This degradation enables subsequent interventional procedures such as re-stenting or arterial surgery to be performed. It is also known that some bioabsorbable and biodegradable materials tend to have excellent biocompatibility characteristics, especially in comparison to most conventionally used biocompatible metals. Another advantage of bioabsorbable and biodegradable stents is that the mechanical properties can be designed to substantially eliminate or reduce the stiffness and hardness that is often associated with metal stents. This is beneficial because the metal stent stiffness and hardness can contribute to the propensity of a stent to damage a vessel or lumen. Examples of novel biodegradable stents include those found in U.S. Pat. No. 5,957,975, which is incorporated by reference in its entirety.

Under the previously employed procedure(s), the metallic and biodegradable stents would be rapidly expanded to balloon nominal diameter of (coronary balloon) from typically 2.0 mm to 5 mm; (vascular peripheral balloon (PTA)) from typically 3 mm to more than 20 mm depending on balloon diameter. From this initial expansion, the stent would often then modulate its diameter. For example, for a 3 mm balloon, the biodegradable stent—educated at a diameter of 3.2—would be expanded to 3 mm and when the balloon was removed, then gradually expand over hours and/or days to 3.2 mm. Rapid expansion, which is typical in the prior art of implanting stents, however, can adversely affect the mechanical properties of polymer and biodegradable stents.

Still others have contemplated deployment by heating polymer and biodegradable stents; however, again, a quick heating process can damage the mechanical properties of the stent and in the case of polymeric stents educated to specific diameter, heating can erase the pre establish education of a preprogrammed desired final diameter. It is desirable to avoid the time that a stent is exposed to adverse temperature conditions (i.e., greater than body temperature—37 degrees C.), thereby enabling greater memory retention of the polymers diameter.

The mechanical property damage that occurs during current stent deployment may contribute to known polymer and biodegradable stent problems. For example, testing in animals has shown that polymer and biodegradable stents still suffer from multiple complications, including breaking of stent struts, complete longitudinal severing of the stent resulting in complete loss of mechanical integrity and collapse of the stent, relaxation-related negative recoil, lack of sufficient radial strength, difficulty in deployment, and distal migration of the entire stent or portions thereof. These failures may lead to thrombosis and occlusion of the vessel being stented with dire consequences for the patient.

Accordingly, it is desirable to find novel stent deployment methods that minimize the potential damage to the stent. As such, the inventors have found a novel method to deploy the stent by use of various stepwise procedures of increasing the pressure/diameter over time to slowly increase the stem diameter and allowing for a period between the stepped increases in pressure/diameter for the stent to acclimatize to its current diameter and stent wall stresses and strains.

BRIEF SUMMARY OF THE INVENTION

The inventors have discovered novel methods of deploying polymeric stents—biodegradable or non biodegradable—by use of stepwise increases in the pressure placed upon the inner diameter of the stent to slowly increase the stent diameter. Previous customary methods of stent deployment may damage the shape and mechanical properties of the stent and may result in complete mechanical failure of the stent. As such, the applicants have invented methods of deployment whereby the stent is inflated in a stepwise process with intervening period of stasis when balloon pressure and diameter are maintained static for a period of time.

BRIEF DESCRIPTION OF THE DRAWINGS

FIG. 1 shows a method of increasing the diameter of the stent in accordance with one preferred embodiment of the invention.

DETAILED DESCRIPTION OF THE INVENTION

Definitions

"Bioresorbable polymer" as used herein refers to a polymer whose degradation by-products can be bio-assimilated or excreted via natural pathways in a human body.

"Acetone bath" as used herein refers to a bath comprising one or more solvents, where the solvents may be acetone, chlorinated hydrocarbons, and/or ketones. The polymeric stent fabrication method includes partially or fully immersed the polymeric stent into the acetone bath.

"Crimping" as used herein refers to a process that involves radial pressing on a polymeric cylindrical device having slits, or openings in the wall thereof to allow a decrease in the diameter of the device without substantially affecting the thickness of the wall or struts of the cylindrical device. Such process, typically also results in an increase in length of the cylindrical device.

"Degradable polymer" or "biodegradable polymer" as used herein refers to a polymer that breaks down into monomers and oligomers when placed in a human body or in an aqueous solution and maintained under conditions of temperature, osmolality, pH, etc., that mimic physiological media preferably without involving enzymatic degradation to minimize the risk of triggering the antigen antibody defense system of the human body.

"Final predetermined shape and diameter" as used herein refers to the desired diameter, length, design and wall thickness of a stent that has been deployed to a target site in a vessel, particularly a blood vessel, duct, or tube in a mammalian subject, particularly a human subject.

"Negative recoil" as used herein refers to an undesirable decrease in the size or diameter of an expanded stent after initial deployment.

"Positive recoil" as used herein refers to an increase in the size or diameter of a stent that has been educated to have a desired final diameter but has not been fully expanded to the desired final diameter.

"Relaxation-related recoil" as used herein refers to the slow change in dimensions of a polymeric device due to a time-dependent slow rearrangement of molecule conformations according to a well-known behavior of viscoelastic polymeric matters. Such rearrangement is due to thermal agitation that slowly leads the polymeric material to a thermodynamic equilibrium typical of the storage conditions when it has been processed under different environmental conditions. Relaxation is very slow below Tg, i.e., when the matter is in the glassy state.

"Tg" or "glass transition temperature" as used herein refers to the temperature at which a polymer changes from a rubbery state to a glassy state and vice versa.

The inventors have discovered novel methods of deploying biodegradable and non biodegradable polymeric stents by use of stepwise increases in the pressure placed upon the inward diameter of the stent to slowly increase the stent diameter. Previous methods of stent deployment may damage the shape and mechanical properties of the stent. As such, the applicatnts have invented a method of deployment whereby the stent is expanded by a slow, stepwise process and thus maintains its mechanical integrity and shape.

I. Exemplary Stent Fabrication and Properties

The stents may be formed from any biodegradable, biocompatible, bioresorbable polymer, preferably a thermoplastic polymer. As used herein, a bioresorbable polymer is one whose degradative products are metabolized in vivo or excreted from the body via natural pathways. Preferably, the stent of the present assembly is formed from a degradable and bioresorbable polymer having a Tg at least 8 degrees above 37° C., preferably at least 20 degrees above 37° C. The polymer of the stent can be a homopolymer or a copolymer. Preferably, the stent is formed from a thin layer of one or more amorphous, bioresorbable polymers, i.e., the polymers used to form the stent preferably are not crystalline. It is also preferred that the polymers used to form the stent do not generate crystalline residues upon degradation in viva. It is also contemplated that the chains of the polymer may be or may not be cross-linked. Light cross-linking, however, is acceptable if thermal and viscoelastic characteristics that allow education, crimping, and deployment of the device are sufficiently maintained.

Appropriate biodegradable polymers may include, but are not limited to, poly(L-lactide), polyglycolide, poly(D,L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes. Examples of the types of polymers that are suitable for the stent of the present invention include, but are not limited to, lactic acid-based stereocopolymers (PLAx copolymers composed of L and D units, where X is the percentage of L-lactyl units) (55<Tg<60), copolymers of lactic and glycolic acids (PLAxGAy, where X, the percentage of L-lactyl units, and Y, the percentage of glycolyl units, are such that the Tg of the copolymer is above 45° C.), and Poly(lactic-co-glycolic-co-gluconic acid) where the OH groups of the gluconyl units can be more or less substituted (pLAx-GayGLx, where X, the percentage of L-lactyl units, and Y, the percentage of glycolyl units, and Z the percentage of gluconyl units are such that the Tg of the terpolymer is above 45° C.). Other suitable polymers include, but are not limited to, poly-lactic acid (PLA), polyglycolic acid (PGA) polyglactin (PLAGA copolymer), polyglyconate (copolymer of trimethylene carbonate and glycolide, and a copolymer of polyglycolide or lactide acid or polylactic acid with ε-caprolactone), provided that the polymer has a glass transition temperature, Tg, of at least 45° C. or greater.

In one preferred embodiment, the stent comprises a polylactic acid stereocopolymer produced from L and DL lactides. The polymer is designated herein as "PLAX" where X represents the percentage of the L-lactic acid units in the mixture of monomers used to prepare the lactides. Preferably X is in the range of 10 to 90, more preferably 25 to 75. In another preferred embodiment, the stent comprises a polylactic acid, glycolic acid copolymer produced from L and DL lactides and glycolides. The polymer is designated herein as "PLAXGAY" where Y represents the percentage of glycolic acid units in the mixture of monomers used to prepare the copolymers. Preferably, the copolymers do not contain glycolyl repeating units since such units are known to be more inflammatory than lactyl repeating units. Preferably, the polymers are prepared using Zn metal or Zn lactate as initiator. To ensure good initial mechanical properties of the stent, the molecular weight of the polymer in the region having the second in vivo lifetime is preferably above 20,000 daltons, more preferably 100,000 daltons or larger. The polydispersity, $I=Mw/Mn$, is preferably below two and should not greatly reflect the presence of low molecular weight oligomers smaller than 2,000 daltons as determined by size exclusion chromatography.

In one embodiment of the invention, a two-dimensional polymer sheet is rolled into a three-dimensional cylindrical stent. For instance, the polymer sheet may be formed by use of a waffle mold. The use of a waffle mold would result in a flat, two dimensional sheet of polymer that is then released from the mold, where the pattern of the mold has resulted in a pattern of struts. The two ends of the two dimensional sheet are then glued together. In another embodiment, the sheet formed by the two-dimensional mold has at least one edge having one or more tongues or strings projecting from the edge which add support to the glued edges and help prevent the three-dimensional cylinder from unrolling into a two-dimensional sheet. The tongues or strings are placed upon the edges and then the edges of the two dimensional sheet of polymer are glued together to form a cylinder shape. In another preferred embodiment, the stent is a formed by a two-dimensional mold that has one edge having one or more slots and tongues comprising a catch or locking mechanism proximate the longitudinal edge thereof.

In another preferred embodiment, the stent is created by use of a three dimensional mold, whereby the inner diameter of the mold is formed by use of a cylindrical rod. It is further contemplated that a metal stent be used to create a reverse mold of the stent. Once the reverse mold is formed, it may be used to make biodegradable stents having the pattern of the metal stent. The resulting mold would be capable of producing stents very quickly. In another embodiment, the stent may be formed by molding or injection molding of the biodegradable material into a three-dimensional mold.

It is further contemplated that any step of the discussed methods of stent production be automated. In one preferred embodiment, all steps of the methods of stent production are automated.

Optionally, the polymeric layer used to make the stent impregnated with an anticoagulant agent, such as heparin, anti-oxidants, such as vitamin E, compounds that regulate cellular proliferation, or anti-inflammatory drugs, such as corticosteroids, to provide localized drug delivery. Such drugs are incorporated into the polymeric layer using techniques known in the art. Agents may also be incorporated into the base polymer that forms the body of the stent, as long as the incorporation does not have significant adverse effects on the desired physical characteristics of the stent such as during radial stent deployment and degradation time. For intravascular stems, it is preferred that the film has a thickness of from about 0.05 mm to 0.2 mm.

Further, in some embodiments, the stent may be coated with or the polymer of the stent may comprise compounds that modulate wound healing. Generally, compounds that modulate wound healing may be any compound that cross links with fibrin to provide matrix for cell adhesion and migration; functions as an early component of the extracellular matrix or assists in matrix formation; binds to collagen and interacts with matrix glycosaminoglycans; has chemotactic properties for macrophages, fibroblasts and endothelial and epidermal cells; promotes opsonization and phagocytosis; forms a component of the fibronexus; forms scaffolding for collagen deposition; or functions otherwise to promote healing.

Examples of compounds that promote wound healing include, but is not limited to, proteases; vasoactive substances such as serotonin and histamine; fibronectin; collagenases; plasminogen activator; neutral proteases; elastin; collagens; proteogycans such as chondroitin-4-sulfate, denuaten sulfate and heparin sulfate; sulfated and non-sulfated glycosaminoglycans; epidermal growth factor (EGF); hormones such as estradiol, testosterone or progesterone; macrophage derived growth factor (MDGF); platelet derived growth factor (PDGF); thrombin; insulin; certain lymphokines; vascular endothelial growth factor (VEGF); fibroblast growth factors; co-factors such as iron, copper, and vitamin C; adrenomedullin; angiogenin; angiopoietin-1; angiopoitin-related growth factor; brain derived neurotrophic factor; corticotropin-releasing hormone; Cyr16; erythropoietin; follistatin; hepatocyte growth factor; interleukins (IL-3, IL-8); midkine; neurokinin A; neuropeptide Y (NPY); pleiotrophin; progranulin; proliferin; secretoneurin; substance P; transforming growth factor; VG5Q; factors that recruit pericytes; and becaplermin.

Generally, the struts are arranged in patterns that are designed to contact the lumen walls of a vessel and to maintain patency of the vessel thereby. A myriad of strut patterns are known in the art for achieving particular design goals.

It is contemplated that a stent may incorporate slits or open spaces to allow for the crimping to temporary reduction in diameter of the cylindrical tube without substantially altering the wall thickness. Moreover, a stent embodying the present invention can include teeth and corresponding catching structure that operates to maintain an expanded form. Moreover, polymer based stents embodying structure defined by a wire or ribbon coil or helix or a knitted mesh configuration are possible examples of self-expanding stents. Other important design characteristics of stents include radial or hoop strength, expansion ratio or coverage area, and longitudinal flexibility. One strut pattern may be selected over another in an effort to optimize those parameters that are of importance for a particular application.

It is also contemplated that the biodegradable stent may have a programmed pattern of in vivo degradation. Stent polymeric structure allows for differential speed degradation. See, for example, U.S. Pat. No. 5,957,975, the entirety of which is incorporated by reference. In one embodiment, the stent comprises at least one substantially cylindrical element having two open ends and a plurality of regions circumferentially spaced around the cylindrical element and extending from one open end to the other open end of the cylindrical element. Each of the regions is configured or designed to have a desired in vivo lifetime. At least one of the regions is designed to have a shorter in vivo lifetime than the other region or regions. This means that the region having the shorter in vivo lifetime degrades sooner after deployment than the regions having a longer in vivo lifetime. Thus, when stents designed in accordance with the present invention are deployed within the lumen of a vessel of a patient, the cylindrical element acquires one or more fissures which extend from one open end of the cylindrical element to the other open end of the cylindrical element within a desired, predetermined period of time after the stent is deployed in the patient. It has been determined that such dismantling, or fragmentation, within a predetermined period of time after deployment allows for enlargement of the lumen of the vessel via the process of arterial remodeling.

The regions of the stent with the different in vivo lifetimes can be made in a variety of ways. Preferably, such stents are made by producing regions having a first in viva lifetime, i.e., a shorter in viva lifetime, in a polymeric layer having the predetermined second, or longer, in vivo lifetime. The regions having the first in viva lifetime are produced by heating the respective regions of the polymeric layer having a second in vivo lifetime for a time and at a temperature sufficient to cause local partial degradation of the polymeric chains. Such treatment, which can be accomplished using a piloted hot needle, laser beam, or flow of hot air, renders the polymer in the heated region more sensitive to hydrolytic degradation. Alternatively, the regions having a first in vivo lifetime may be produced in a polymeric layer having a second in vivo lifetime by incorporating a sufficient number of acidic ions into the respective regions of the polymeric layer. Preferably, the acidic ions are provided by compounds that are not soluble in blood.

Regions having a first in viva lifetime can also be produced in a polymeric film having a second in viva lifetime by exposure of the respective regions to beta radiation or gamma radiation for a sufficient time to induce partial cleavage of the polymeric chains within the respective regions. Provided the polymeric layer has a thickness of less than 0.3 mm, regions having a first in vivo lifetime can also be produced in a polymeric film having a second in vivo lifetime by introducing areas of mechanical weakness into the polymer. One method of introducing mechanical weakness is by reducing the thickness of the polymer in the respective region or forming holes therein. Regions having a first in vivo lifetime can also be produced in a polymeric film having a second in vivo lifetime by applying mechanical stress to the respective region. However, this latter process is difficult to control and, thus, is less preferred. Differing lifetimes can also be created by providing one or more different coatings over different regions of the biodegradable stent.

The initial polymeric cylindrical device that is formed by any of these processes can be configured to have the final predetermined shape, length, wall thickness and diameter, all of which are tailored to the application for which the stent is to be utilized. For example, for cardiovascular applications the initial polymeric device that is formed by these processes can have a final predetermined length ranging from 0.5 cm to approximately 3 cm. For certain applications, the initial polymeric cylindrical device can have a final, predetermined diameter ranging from 0.50 mm to 8.0 mm with a final, predetermined wall thickness ranging from 0.05 to 0.5 mm. Alternatively, the initial cylindrical device that is formed by any of these processes can have a smaller diameter than the final predetermined diameter.

In those instances where the initial polymeric cylindrical device has a smaller diameter than the final predetermined diameter, slits or openings are formed in the cylindrical device as described above, and then the cylindrical device is deformed or expanded to the final shape and diameter. This can be achieved by inserting an expandable device such as a balloon into the stent.

In one embodiment, once the stent is formed, the stent is immersed in a bath comprising at least acetone and then dried. Immersion of the stent into the bath decreases the sharp surfaces and irregularities, as determined by scanning electron microscopy. The stents can be dried by any means, but preferably, the stents are dried at atmospheric pressure until they achieve a constant weight. Complete drying may be verified by measuring the residual acetone by gas chromatography or by thermo gravimetric analysis.

The acetone bath step would be generally conducted at a temperature that is below the glass transition temperature of the polymer that forms the stent. Preferably, the acetone bath step is conducted at a temperature of below 65° C., more preferably below 60° C., most preferably below 55° C. In certain embodiments, a temperature below about 50° C. is most preferred. It is preferable to use a temperature that is below the glass transition temperature of the stent as this results in reducing the exposure of the stent to adverse temperature conditions.

If the surface tension of the solvent used in the solvent bath is too high, it may inhibit solvent entry into the inner surface of the stent, leading to variation in the properties of the stent over its length. If desired, this can be avoided by manipulation of the atmospheric pressure over the solvent bath, adding agents to the bath to reduce the surface tension of the solvent, agitation or altering flow through the lumen of the stem.

The acetone concentration in the bath can be any concentration determined by one skilled in the art to decrease the sharp edges and irregularities of the stent, decrease the surface reactivity of the stent, and/or decrease the reactive amino groups. It is preferred that the polymer dissolved in the acetone bath has a concentration of at least about 0.05% weigh/volume, and is most preferably at least about 5% weight volume.

In addition, certain embodiments of the invention provide for the addition of poly(lactic) acid (PLA), poly-L-lactide, poly-DL-lactide, L-lactide monomers and/or DL-lactide monomers to the acetone bath. It is further contemplated to add one or more polyethers to the acetone bath. It is contemplated that the polyethers may include, but is not limited to, polyethylene glycol, polyethylene oxide, crown ethers, or mixes thereof. Preferably, the polyether added to the acetone bath is polyethylene glycol (PEG). In one preferred embodiment, the acetone bath contains PLA-PEG diblock copolymers. The concentration of PLA and/or PLA-PEG diblock copolymers is greater than about 0.1% weight/volume, preferably greater than about 10% weight/volume, and more preferably about 5% weight/volume. It is also understood that the acetone bath may contain other polymers, compounds and/or chemicals that are also included in the composition of the stent. For instance, if the stent polymer contains a biodegradable polymer such as polycaprolactone, polyglycolide, poly-3-hydroxybutyrate, polyglycolide, poly(D,L-lactide), copolymers of lactide and glycolide, polycaprolactone, polyhydroxyvalerate, polyhydroxybutyrate, polytrimethylenecarbonate, polyorthoesters, polyanhydrides, polyphosphazenes, or mixes thereof, the polymer(s) may also be added to the acetone bath.

Further, it is contemplated that other solvents may be used instead of acetone or may be included with the acetone in the bath. For instance, solvents that may be used in the bath includes one or more types of chlorinated or halogenated hydrocarbons. The chlorinated hydrocarbons contemplated includes, but is not limited to dichloromethane, 1,1,1-trichloroethane, 1,1,2-trichloroethane, 1,1-dichloroethane, trichloroethlene, lindane, polychlorinated biphenyls, dioxins, furans, perchloroethylene, chloroform, methoxychlor, hexachlorocyclohexane, chlordane, dieldrin, heptachlor, methoxychlor, toxaphene, carbon tetrachloride, or mixtures thereof.

It is also contemplated to use solvents from the ketone family instead of acetone or included with acetone in the bath. Members of the ketone includes organic compounds that contain a carbonyl group that is bonded to only carbon atoms. The ketones contemplated includes, but is not limited to: acetoacetate, acetophenone, butanone, C-11 ketone, cyclohexanone, diacetone alcohol, diisobutyl ketone, isophorone, methyl amyl ketone, methyl ethyl ketone, methyl isoamyl ketone, methyl isobutyl ketone, beta-hydroxybutyrate, or mixes thereof. Other useful solvents and mixtures thereof that can be utilized in the baths include the aldehydes, which could also help to stabilize certain polymers used in the stents.

In some embodiments, drugs or compounds that modulate coagulation or wound healing may be added to the bath. Further, the step of the acetone bath can occur at any point during the fabrication of the stent. Preferably, the step of the acetone bath occurs at the end of the stent fabrication. More preferably, the step of the acetone bath occurs before the stent is educated.

II. Exemplary Educating and Crimping of the Stent

While it is at the final predetermined shape, size, and diameter, the cylindrical device is educated by heating the device to a temperature above the Tg of the polymer from which the device is formed. The device is heated for a time sufficient to erase former process-related memory and to impart a new memory of the final predetermined shape and diameter to the polymeric cylindrical device. It is believed that such conditions allow the polymer chains to relax and reorganize themselves from an entanglement typical of the former processing stages to an entanglement typical of the high temperature at which the cylindrical device is compatible with the final or deformed shape and size. When the polymeric cylindrical device has an initial diameter that is less than the final predetermined diameter, it is desired to heat to a temperature well above the Tg of the polymer. This heating step erases the anisotropic stresses promoted by the extrusion or molding process and the former processing-related memory of the polymer chains. Good results have been obtained by heating a laser-precut polymeric cylindrical device formed from PLA75 and deformed from a diameter of 1.0 mm to 4 mm at a temperature of 80° C. for 30 minutes. Temperatures of from about 45° C. to about 120° C. and times of 5 minutes or more should be suitable for educating stents made from PLAx with $0<X<100$, PLAxGAy with $0<X<25$ and $75<Y<100$, or any PLAxGAyGLz. The polymeric cylindrical device is then crimped.

To crimp the educated cylindrical device, the educated cylinder device is mounted onto a different device with a smaller diameter. The diameter of the educated cylinder is reduced by heating the cylinder to a temperature below the Tg of the polymer while evenly applying pressure on the exterior surface of the wall of the cylindrical device. Such evenly applied pressure can be obtained by a variety of methods, including the inflation of a balloon with an inner cylindrical hole that decreases in diameter as the balloon is inflated.

The polymeric stent is crimped onto any device that may be used to expand the stent by increasing the stent inner diameter. In one embodiment, the stent is crimped onto an inflatable device such as an inflatable balloon catheter. In this instance, the stent assembly after crimping comprises an inflatable balloon catheter and an expandable, educated, polymeric stent snugly and stably disposed thereon. Slits or open spaces that allow for a reduction in diameter of the cylindrical device without substantially altering the wall thickness during crimping are incorporated into the cylindrical device prior to the time the cylindrical device is crimped on the inflatable balloon catheter. The temperature at which the cylindrical device is heated during crimping is high enough to allow reduction in diameter of the cylindrical device but low enough to not erase the memory of the final predetermined shape and diameter of the educated cylindrical device. Ideally, the temperature is less than the glass transition state of the polymer. More preferably, the temperature is at about 50° C. Thus, the temperature at which the educated cylindrical device is heated during crimping is less than the temperature at which the cylindrical device is heated during education of the cylindrical device. Further, the time it takes to crimp the educated cylindrical device can vary, depending upon the temperature, size and composition of the stent.

In accordance with the present method, expansion of the diameter of the polymeric stent can be achieved by any means. In one preferred embodiment, the balloon that the scent is crimped upon is inflated and/or heated to initiates the stent expansion. It is contemplated that the positive recoil properties of the stent contribute to expanding the stent to its final predetermined diameter. The temperature used to initiate the stent expansion may be any temperature at or below the Tg of the polymer, preferably the temperature is about body temperature. In a less preferred embodiment, a balloon is inflated to expand the polymeric stent to its final predetermined shape.

In another aspect, the method of the present invention starts with a polymeric tube whose diameter initially is less than the final predetermined diameter. Such tube is first heated to a temperature close to or above the Tg of the polymer and expanded to provide a cylindrical device whose diameter is equal to the final desired diameter. Thereafter the cylindrical device is educated as described above to provide an educated cylindrical device having a memory of the final predetermined shape and diameter, and then crimped on a balloon catheter as described above to provide an assembly comprising the balloon catheter and an expandable, educated, polymeric stent snugly and stably disposed thereon.

The present invention also provides an assembly comprising an inflatable balloon catheter and a polymeric stent prepared in accordance with the present method.

Preferably, the stent of the present invention exhibits little to no relaxation-related negative recoil when deployed in the blood vessel of a subject. Advantageously, the assembly of the present invention has a diameter that allows it to be easily inserted into a blood vessel of the subject and advanced to a target site. In one embodiment, the stent of the present invention exhibits expansion (positive recoil) and adaptation to the geometry of the artery when the stent is not fully deployed up to its final diameter during deployment. Positive recoil over several days will create outward radial pressure for long periods of time. This outward radial pressure aids in positive vascular remodeling by assisting stabilizing the injured artery or vulnerable plaque, assist in cellular progress to repair injury of original acute expansion, assist in security of tissue flaps, and the like.

In addition, in a preferred embodiment, the stent of the present invention is stably disposed on the balloon, meaning that a mechanical restraint is not required to prevent the stent from rapidly expanding to its final diameter during storage at room temperature. Thus, although not required, the assembly of the present invention, optionally, also comprises a retractable sheath covering the exterior surface of the stent. Such sheath serves to prevent deformation of the scent and preclude or slow expansion during storage.

III. Exemplary Procedures for Determining Times and Temperatures for Educating and Crimping the Stent of the Present Invention Temperatures and times suitable for educating the cylindrical device and for thereby developing a stent that resistant to negative recoil, and in fact has positive recoil, can be assessed by first crimping the stent of the present invention onto a balloon catheter. The balloon is then inflated to initiate stent expansion. The balloon is removed and the stent is stored at 37° C. While in storage, the stent may increase in diameter because of the positive recoil properties of the scent. If the stent exhibits little to no negative recoil when stored under these conditions for 4 to 6 weeks or, preferably the time estimated for an artery wall to recover from PTC angioplasty, the times and temperatures employed for educating the stent are suitable. In those cases where the polymeric stent exhibits a small amount of recoil, the cylindrical device is preferably educated at a diameter slightly larger than the final predetermined diameter to compensate for the small amount of negative recoil.

Temperatures and times suitable for crimping the scent to a reduced diameter can be assessed by allowing the stent-mounted balloon catheter of the present assembly to stay at room temperature or at the storage temperature. If the crimped stent stays collapsed at the small diameter corresponding to the deflated balloon under these conditions, the times and temperatures employed during crimping are suitable.

Optimization of the imparted stent mechanical properties such as positive recoil can be achieved by storing the finished product at a room temperature below 20° C. Preferably, the finish product is refrigerated at about 6° to 8° C.

IV. Deployment of the Stent

The deployment of the polymer-based scent can occur by a variety of processes. One preferred deployment method involves a stepwise process. First, the scent is allowed to reach the body temperature of about 37° C. The preheating of the scent can occur by any means, including heating in saline, the in vivo blood stream, or hot air. The amount of time it takes to heat the stent is dependent upon the design and manufacture if the stent. In one preferred embodiment, the preheating step takes 60 to 300 seconds. Before, during or after the preheating period, the polymer-based stent assembly of the present invention is introduced into a duct, tube, or vessel, e.g. a blood vessel of a mammalian subject, preferably in conjunction with a guiding catheter, and advanced to a target site, e.g., the site of stenotic lesion. After it is located at the target site the balloon, or other inflationary device, slowly applies pressure to the interior diameter of the stent. The pressure on the stent results in an increase in the diameter of the stent. The stent is expanded until the first expansion is detected by fluoroscopy. The pressure is maintained at this level, i.e. no further expansion, for a time sufficient for the stent to acclimate to its new diameter. As a second step, the pressure is gradually increased to a slightly higher pressure. The pressure is maintained at this level for a period of time sufficient for stent acclimation. This step is repeated until the final desired diameter is reached.

The time sufficient for acclimation at each step may vary depending upon the stent design and manufacture. In one preferred embodiment, the time sufficient for acclimation is about 10 to 20 seconds. Further, it is preferred that for each step the pressure increase at about one atmosphere. The number of step necessary to fully deploy the stent to its final desired diameter varies depending upon the stent characterization and the inward mechical forces of the arterial wall, but the minimum time for the entire process should at least about fifty seconds.

Once the final desired diameter is reached, the pressure is maintained for a period of 30 to 60 seconds to enable the stent to acclimate to its deployment diameter. The balloon or other deployment device is deflated or otherwise changes configuration to enable deployment of the stent and retraction of the balloon or deployment device. The stent will then continue to expand over hours or days to its final educated diameter Preferably, the stent is not inflated beyond its final desired diameter, which is determined by the education of the stent].

In a preferred embodiment, the fracturing of the plaque occurs before the stent deployment. Thereafter, the stent is introduced into the desired site on a separate catheter, preferably an expanding balloon catheter.

FIG. 1 shows one preferred embodiment of the invention. The stent assembly device comprising a stent and an inflationary or expansion device such as a balloon or other deployment device are first inserted within the body at step 101. The stent is allowed to reach the temperature of about 37° C. at step 102. Preferably, this occurs over about 60 to 300 seconds. The inflationary device then applies approximately one (1) atmosphere of pressure onto the interior diameter of the stent at step 103. This pressure is held constant until the stent acclimates to the new diameter at step 104. Preferably, the pressure is held constant for about 10 to 20 seconds. At this time, the clinician deploying the stent must determine if the final diameter of the stent has been reached at step 105. If the diameter of the stent is less than the final desired diameter, then steps 103 through 105 are repeated. If at step 105 the final predetermined diameter is reached, the pressure is held at step 106 until the stent is fully acclimated to the deployment diameter, preferably about 30 to 60 seconds. The inflationary device is then removed.

The diameter and placement of the stent may be determined by any means. In one embodiment, part or all of the stent is coated or wrapped with a radiopaque material to allow real time visualization of the stent by the cardiologist or interventional radiologist. Gold is often the radiopaque material preferred because gold is non-irritating and substantially non-allergic. Further, gold offers high fluoroscopic visibility in a very thin layer and is believed to decrease thrombus formation.

In a preferred embodiment, the stent comprises at least two markers placed such that the diameter of the stent may be determined in real time. This feature helps to determine if the stent has been properly expanded. The placement of such markers may also determine at any time if the diameter of the stent has increased or decreased.

The methods to detect the marker may include, but is not limited to, x-ray, magnetic resonance imaging (MRI), and ultrasound. The markers may be used to track the location of the stent as it travels through the body. This greatly assists the physicians in determining if the stent is traveling the correct path through the vasculature. This further assists the physician in placing the stent at the correct site within the lumen.

It is also contemplated that the stent may comprise at least three markers. The use of at least three markers enables the three dimensional location of the stem to be determined at any time. This feature greatly assists to ensure that the stent does not have rotational motion within the lumen. Rotational motion may occur if the outer diameter of the stent is less than the inner diameter of the vessel that the stent is placed within. This may indicate that the diameter of the stent needs to be increased. Rotational motion of the stent within the lumen is disfavored because it increases blood flow turbidity, which increases thrombogenesis.

The marker may be any material that is visible within the body by an external means, including but limited to x-ray and MRI. In one embodiment, the stent of the present invention achieves MRI visibility by use of a marker that generates a magnetic susceptibility artifact such as a paramagnetic, ferromagnetic, non-ferromagnetic, ferromagnetic, or superparamagnetic substance. In another embodiment, the test of the present invention achieves visibility by x-ray by use of a radiopaque marker.

Moreover, the markers may be applied to the stent in any number of ways, including but limited to, application as a ribbon that is crimped onto a strut of the stent and a partially sputter heavy metal coating.

In addition to coronary arteries, the present stent may be used in other arteries such as for example, femeroiliac arteries, the carotid artery, vertebro-basilar arteries, as well as in the interior of other hollow passageways such as for example veins, ureters, urethrae, bronchi, biliary and pancreatic duct systems, the gut, eye ducts, and spermatic and fallopian tubes. Indeed, it is further contemplated that certain aspects of the present invention include devices that are used as substitutes for veins, arteries, and ductal or tubal structures in the body.

While only the presently preferred embodiments have been described in detail, as will be apparent to those skilled in the art, alternatives, additions, modifications and improvements may be made to the device and method disclosed herein without departing from the scope of the invention. Accordingly, it is not intended that the invention be limited, except as by the appended claims.

We claim the device and methods as set forth above.

What is claimed is:

1. A method for deploying a polymeric stent, said method comprising:
   I) increasing the temperature of the stent to about 37° C. for a period of time;
   II) positioning the stent in a duct or vessel;
   III) increasing the pressure on the interior diameter of the stent;
   IV) detecting the stent expansion; and
   V) maintaining the same pressure on the interior diameter of the stent for a period of time, without further expanding the stent, so that the stent acclimates;
   repeating steps (III) through (V) until the stent is at its final desired deployment diameter, and wherein step (II) may occur before, during or after step (I);
   wherein the temperature of the stent is maintained below its glass-transition temperature throughout steps (II)-(V).

2. The method of claim 1, wherein step (I) further includes increasing the temperature of the stent to about 37° C. for at least about 60 seconds.

3. The method of claim 1, wherein step (V) further includes maintaining the same pressure on the interior diameter of the stent for at least 10 seconds, without further expanding the stent, so that the stent acclimates.

4. The method of claim 1, wherein the polymeric stent includes at least one biodegradable polymer.

5. The method of claim 4, wherein the at least one biodegradable polymer is selected from the group consisting of poly(L-lactide), polyglycolide, poly(D,L-lactide), copolymers of lactide and glycolide, polycaprolactone, polyhydroxyvalerate, polyhydroxybutyrate, polytrimethylenecarbonate, polyorthoesters, polyanhydrides, polyphosphazenes, polylactic acid, polyglycolic acid, polyglactin, polyglyconate, lactic acid-based stereocopolymers, copolymers of lactic and glycolic acids, and Poly(lactic-co-glycolic-co-gluconic acid).

6. The method of claim 5, wherein the polymeric stent comprises poly(lactic) acid-polyethylene glycol (PLA-PEG) diblock co-polymers.

7. The method of claim 6, wherein the PLA-PEG diblock co-polymers are surface modifying agents.

8. The method of claim 1, wherein the glass transition temperature is at least 37° C.

9. The method of claim 1, wherein the glass transition temperature is at least 45° C.

10. The method of claim 1, wherein the glass transition temperature is at least 57° C.

11. The method of claim 1, wherein the polymeric stent further comprises an anticoagulant agent or anti-inflammatory drug.

12. The method of claim 11, wherein the anticoagulant agent or anti-inflammatory drug is selected the group consisting of heparin, anti-oxidants, vitamin E, compounds that regulate cellular proliferation, and corticosteroids.

13. The method of claim 1, wherein the polymeric stent further comprises at least one compound that modulates wound healing.

14. The method of claim 13, wherein the at least one compound that modulates wound healing is selected from the group consisting of: proteases; vasoactive substances such as serotonin and histamine; fibronectin; collagenases; plasminogen activator; neutral proteases; elastin; collagens; proteogycans such as chondroitin-4-sulfate, dermaten sulfate and heparin sulfate; sulfated and non-sulfated glycosaminoglycans; epidermal growth factor (EGF); hormones such as estradiol, testosterone or progesterone; macrophage derived growth factor (MDGF); platelet derived growth factor (PDGF); thrombin; insulin; certain lymphokines; vascular endothelial growth factor (VEGF); fibroblast growth factors; co-factors such as iron, copper, and vitamin C; adrenomedullin; angiogenin; angiopoietin-1; angiopoitin-related growth factor; brain derived neurotrophic factor; corticotropin-releasing hormone; Cyr16; erythropoietin; follistatin; hepatocyte growth factor; interleukins (IL-3, IL-8); midkine; neurokinin A; neuropeptide Y (NPY); pleiotrophin; progranulin, prolifern; secretoneurin; substance P; transforming growth factor; VG5Q; factors that recruit pericytes; and becaplermin.

15. The method of claim 1, wherein the polymeric stent is increased to the temperature in step (I) by use of heating in saline, the in vivo blood stream, or hot air.

16. The method of claim 1, wherein the stent is increased to the temperature in step (I) for a period of time sufficient to transfer enough energy to allow chain mobility in step (III).

17. The method of claim 16, wherein the period of time is about 60 to 300 seconds.

18. The method of claim 1, wherein step (I) occurs before step (II).

19. The method of claim 1, wherein step (III) occurs by use of an inflationary device.

20. The method of claim 1, wherein step (III) occurs by use of heat transferring fluid.

21. The method of claim 1, wherein step (IV) occurs using medical imaging technology.

22. The method of claim 1, wherein the increase in pressure of step (III) is an increase in one atmosphere.

23. The method of claim 1, wherein the time for the entire method to occur is at least fifty seconds.

24. A method for deploying a polymeric stent, said method comprising:
   I) increasing the temperature of the stent to about 37° C. for a period of time;
   II) positioning the stent in a duct or vessel;
   III) increasing the pressure on the interior diameter of the stent;
   IV) detecting the stent expansion; and
   V) maintaining the same pressure on the interior diameter of the stent for 10 seconds, without further expanding the stent, so that the stent acclimates;
   repeating steps (III) through (V) until the stent is at its final desired deployment diameter, and wherein step (II) may occur before, during or after step (I);
   wherein the temperature of the stent is maintained below its glass-transition temperature throughout steps (II)-(V).

* * * * *